(12) United States Patent
Yamamoto et al.

(10) Patent No.: US 8,298,514 B2
(45) Date of Patent: *Oct. 30, 2012

(54) AGENT FOR ENHANCING CONTRAST OF IMAGE OF FLUORESCENT STAINING OF LUMEN OF DIGESTIVE TRACT

(75) Inventors: Akira Yamamoto, Tokyo (JP); Yusuke Iimori, Tokyo (JP); Mizue Saze, Tokyo (JP); Mariko Ishiguro, Tokyo (JP); Pilryon Lee, Tokyo (JP)

(73) Assignee: HOYA Corporation, Tokyo (JP)

( * ) Notice: Subject to any disclaimer, the term of this patent is extended or adjusted under 35 U.S.C. 154(b) by 992 days.

This patent is subject to a terminal disclaimer.

(21) Appl. No.: 11/762,961

(22) Filed: Jun. 14, 2007

(65) Prior Publication Data

US 2008/0008656 A1 Jan. 10, 2008

(30) Foreign Application Priority Data

Jun. 15, 2006 (JP) ................. 2006-165712

(51) Int. Cl.
*A61B 5/00* (2006.01)
(52) U.S. Cl. ........................................... 424/9.6
(58) Field of Classification Search ............ 424/9.6
See application file for complete search history.

(56) References Cited

U.S. PATENT DOCUMENTS

| 4,945,239 | A | 7/1990 | Wist et al. |
| 2007/0077202 | A1 | 4/2007 | Yamamoto et al. |
| 2007/0172912 | A1 | 7/2007 | Yamamoto et al. |

FOREIGN PATENT DOCUMENTS

| GB | 1113760 | 5/1968 |
| JP | 3244395 | 10/1991 |
| WO | 2005/079204 | 9/2005 |

OTHER PUBLICATIONS

Polglase AL, McLaren WJ, Skinner SA, Kiesslich R, Neurath MF, Delaney PM. A fluorescence confocal endomicroscope for in vivo microscopy of the upper- and the lower-GI tract. 2005 Gastrointest. Endosc. 62: 686-695.*
Beck DE, Fazio VW, Jagelman DG. Comparison of oral lavage methods for preoperative colonic cleansing. 1986 Dis. Colon Rectum. 29: 699-703.*
Giloh H, Sedat JW. Fluorescence microscopy: reduced photobleaching of rhodamine and fluorescein protein conjugates by n-propyl gallate. 1982 Science 217: 1252-1255.*
Torres A, El-Ebiary M, Soler N, Montón C, Fàbregas N, Hernández C. Stomach as a source of colonization of the respiratory tract during mechanical ventilation: association with ventilator-associated pneumonia. 1996 Eur. Respir. J. 9: 1729-1735.*
Golytely® Product Information Sheet (1 page), Nov. 2011.
NIFLEC Product Information Sheet (5 pages), Apr. 13, 2011.
Satoh et al.; Journal of Gastroenterology, 1987, vol. 84, No. 7, pp. 130.
Japan Office action, dated Nov. 1, 2011 along with an english translation thereof.
Winters, Jr. et al., Gastroenterology 92: 118-124, 1987.
Glickman et al., Am J Surg Pathol, 25(5): 569-578, 2001.
Ragunath et al., Endoscopy 35: 998-1003, 2003.
Barrett, Stomach and Intestine, 39(9), 1209-1210, 2004, in Japanese with English translation including pp. 1209-1211.
Inoue et al., Digestive Endoscopy, 14 (5), 565-572, 2002, in Japanese with English translation including pp. 565-581.
Kiesslich et al., Gastroenterology 2004, vol. 127, No. 3, p. 706-713.

* cited by examiner

*Primary Examiner* — Michael G Hartley
*Assistant Examiner* — Jennifer Lamberski
(74) *Attorney, Agent, or Firm* — Greenblum & Bernstein, P.L.C.

(57) ABSTRACT

The present invention provides an agent and a method for enhancing a contrast of an image of fluorescent staining of a lumen of the digestive tract with an intravenously administered fluorescent dye, wherein the agent for enhancing a contrast is an agent for a lumen of the digestive tract containing an aqueous solution having a buffer capacity and having a pH of 6 to 10.

4 Claims, 2 Drawing Sheets

AFTER USE OF AGENT FOR ENHANCING CONTRAST

BEFORE USE

20 TIMES  63 TIMES

AGENT FOR ENHANCING CONTRAST OF IMAGE OF FLUORESCENT STAINING OF LUMEN OF DIGESTIVE TRACT

BACKGROUND OF THE INVENTION

1. Field of the Invention

The present invention relates to an agent for enhancing a contrast, which is intended to clearly show an image of fluorescent staining of a lumen of the digestive tract with a fluorescent dye and raise diagnostic precision.

2. Description of the Related Art

In Europe and America, the onset of reflux esophagitis and Barrett's esophagus as gastroesophageal reflux-related diseases has increased in frequency in recent years. Various therapeutic methods have been developed for Barrett's esophagus, which is closely associated with esophageal adenocarcinoma. The epithelium of the mucosa that covers the internal surface of the esophageal wall is called the stratified squamous epithelium. This stratified squamous epithelium has many layers of cells and is evidently different from the form of the gastric mucosa, which has a simple columnar epithelium structure. Specifically, a site at which the forms of epithelial cells distinctly change is the boundary between the esophagus and the stomach.

Barrett's esophagus develops as a result of a prolonged course of reflux esophagitis caused by an inflammation in the esophageal mucosa due to gastric juice reflux into the esophagus. This disease is characterized in that the columnar epithelium of 3 cm or more in length is consecutively present all around the esophagogastric junction from the gastric side to the esophagus (Gastroenterology 92: 118-124, 1987).

There are only a few pathological reports on a mechanism though which the squamous epithelium is transformed into the columnar epithelium, and much remains to be elucidated. The epithelium within Barrett's mucosa having the morphological and histological features of the squamous and columnar epithelia is called the multilayered epithelium (ME). This epithelium is composed of four to eight layers of cells and is analogous in the deep part thereof to basal cells and in the surface thereof to the columnar epithelium. Furthermore, cytokeratin expression in ME has the natures of both the stratified squamous and columnar epithelia. A theory exists that this ME is a progenitor cell that gives rise to the columnar epithelium of Barrett's esophagus (Am J Surg Pathol 25: 569-578, 2001).

The early detection of a lesion is important for the diagnosis of the gastroesophageal reflux-related diseases. Therefore, the determination of progression of the diseases requires determining the degree of infiltration into tissues. This is because the early detection allows for not surgical resection but endoscopic mucosal resection. Patients who complain of a symptom are subjected to endoscopic observation, and their lesions can be detected easily if having distinct erosion or ulcer to the extent recognizable visually. By contrast, patients who have a symptom such as heartburn but no distinctly observed esophagitis are subjected to a method in which the esophageal pH is monitored for 24 hours. However, this method is psychologically painful for the patients.

The boundary between the stomach and the esophagus in cases of Barrett's esophagus is not easy to determine by usual endoscopic observation using white light sources. Therefore, random biopsy has been conducted to confirm the denaturation of mucosal tissues. However, an affected site or a region, even if diagnosed as cancer by biopsy, is difficult to be identified in many cases. Thus, dye-spraying endoscopy has been practiced, in which methylene blue staining has been used (Endoscopy 35: 998-1003, 2003). However, the methylene blue staining requires completely removing mucus, whereas staining using crystal violet clearly stains Barrett's mucosa but has no clear direct relationship with cancer detection (Stomach and Intestine, 39 (9), 1209-1210, 2004).

Magnifying endoscopes diagnose the depth of invasion by vascular network observation. However, changes in vascular network also differ depending on cancer differentiation and grades as well as on infiltration patterns. Therefore, a possible level of determination by the endoscopes is unknown. The use of the magnifying endoscopes has been said to exceedingly effectively conduct the qualitative diagnosis of cancer or non-cancer and the diagnosis of the depth of invasion (Digestive Endoscopy, 14 (5), 565-572, 2002) and has been reported to improve diagnostic accuracy to 71% as compared with usual endoscopes and dye-spraying endoscopes, which have 45% diagnostic accuracy.

Confocal endoscopes, which has a usual endoscope equipped with a confocal imaging system, can produce a cross-sectional image of biological surface having intricately multilayered cells and connective tissues by detecting a biological tissue suspected of having a lesion by the usual endoscopic observation and observing the tissue by the confocal imaging system. This endoscope serves as means for performing noninvasive diagnosis on the basis of cell forms and tissue forms without collecting the tissues. To obtain the cross-sectional image, a fluorescent substance is usually administered to observed sites.

The fluorescent substance is a substance that emits fluorescence. A better fluorescent substance has less toxicity in vivo.

Thus, fluorescein has conventionally been used as a fluorescent contrast agent safe to living bodies in ophthalmoscopy or the like in which an aqueous solution of fluorescein is intravenously injected.
(Gastroenterology, 127 (3), 706-713, 2004)

However, studies conducted by the present inventor have demonstrated that the intravenous administration of fluorescein and the subsequent fluorescent observation of a lumen of the digestive tract do not produce clear fluorescent staining images in some cases. Further studies conducted by the present inventor have also demonstrated that such cases in which clear fluorescent staining images are not obtained are apparent especially for the upper digestive tract such as the stomach, intestinum duodenum, and esophagus.

Thus, an object of the present invention is to provide means for more clearly showing an image of fluorescent staining of a lumen of the digestive tract with an intravenously administered fluorescent dye.

SUMMARY OF THE INVENTION

Thus, the present inventor has conducted various studies on the cause of the unclarity of an image of fluorescent staining of a lumen of the digestive tract and has consequently found that the unclarity depends on the pH of the lumen of the digestive tract. The present inventor has further conducted studies and has found that the spraying of an aqueous solution having a buffer capacity and having a pH of 6 to 10 to the lumen of the digestive tract and subsequent fluorescent observation remarkably clearly shows the fluorescent staining image. Based on these findings, the present invention has been completed.

Specifically, the present invention provides an agent for enhancing a contrast of an image of fluorescent staining of a lumen of the digestive tract with an intravenously administered fluorescent dye, wherein the agent for enhancing a contrast is an agent for a lumen of the digestive tract containing an aqueous solution having a buffer capacity and having a pH of 6 to 10.

The present invention also provides a method for enhancing a contrast of an image of staining of a lumen of the digestive tract with an intravenously administered fluorescent dye, including applying an aqueous solution having a buffer capacity and having a pH of 6 to 10 to a lumen of the digestive tract in a diagnostic method in which the lumen of the digestive tract is stained by intravenous administration of a fluorescent dye.

The present invention further provides use of a composition for a lumen of the digestive tract containing an aqueous solution having a buffer capacity and having a pH of 6 to 10 for the manufacture of an agent for enhancing a contrast of an image of fluorescent staining of a lumen of the digestive tract with an intravenously administered fluorescent dye.

The agent for enhancing a contrast of the present invention can remarkably clearly shows an image of fluorescent staining of the digestive tract with an intravenously administered fluorescent dye by a simple procedure of spraying or applying the agent for enhancing a contrast to a lumen of the digestive tract. Thus, the use of the agent for enhancing a contrast of the present invention allows for detection of early cancer or the like especially in the upper digestive tract, which has conventionally been difficult to diagnose by fluorescent observation using an endoscope.

DETAILED DESCRIPTION OF THE PREFERRED EMBODIMENTS

Figure 1:
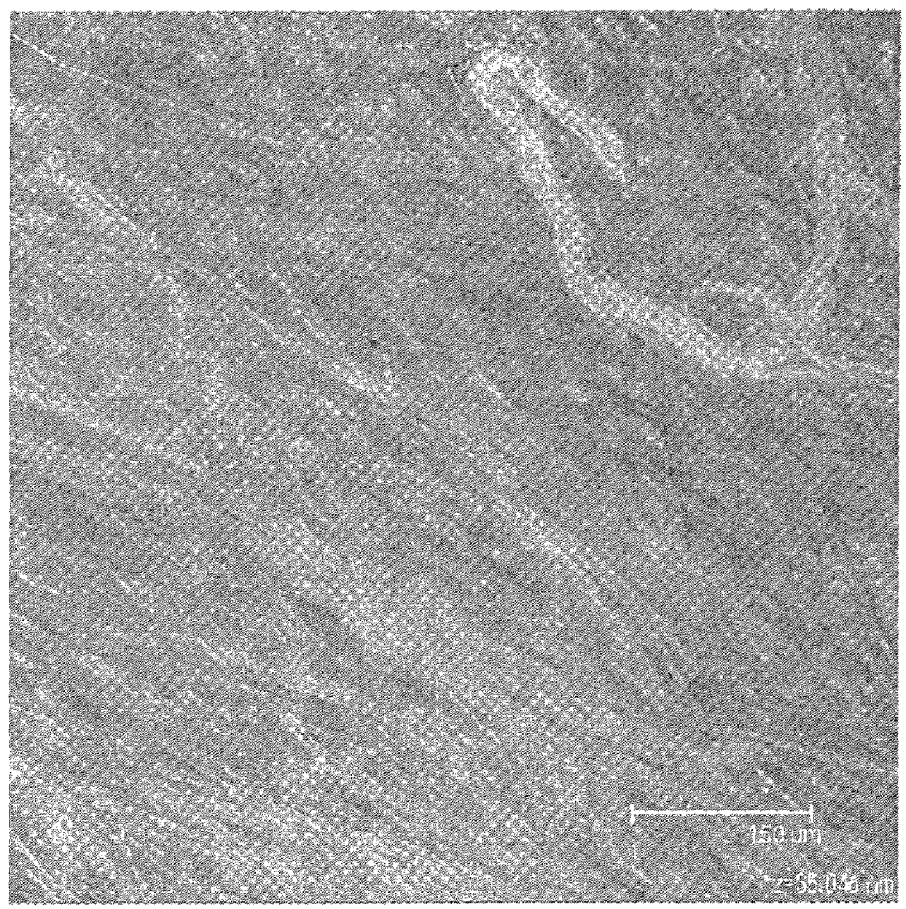
FIG. 1 is a diagram showing an image of fluorescent staining of the esophagus with fluorescein sodium by use of an agent for enhancing a contrast (pH 6) of the present invention.

The present disclosure relates to subject matter contained in Japanese Patent Application No. 2006-165712 filed on Jun. 15, 2006, which is expressly incorporated herein by reference in its entirety.

An agent for enhancing a contrast of the present invention is an agent for a lumen of the digestive tract containing an aqueous solution having a buffer capacity and having a pH of 6 to 10. The aqueous solution having a buffer capacity used in the present invention has a pH of 6 to 10 and preferably has a pH of 6 to 9, particularly preferably a pH of 6 to 8, from the viewpoint of the effect of enhancing a contrast and safety.

Any aqueous solution having a buffer capacity may be used in the present invention as long as its pH can be adjusted to the range of 6 to 10. A variety of acidic and/or basic substances that produce a desired pH within this range may be selected and formulated in the aqueous solution to show a buffer capacity.

Examples of the acidic substances used in the present invention include: inorganic acids such as phosphoric acid, hydrochloric acid, and carbonic acid; and nontoxic organic acids such as acetic acid and citric acid. Examples of the basic substances used in the present invention include sodium hydroxide, sodium acetate, sodium hydrogen phosphate, and glycine. Examples of buffers containing these substances in combination include sodium phosphate, sodium acetate, sodium citrate, sodium carbonate, tris(hydroxymethyl)aminomethane-hydrochloric acid, lysine-hydrochloric acid, and arginine-hydrochloric acid. In the present invention, an aqueous solution containing these buffers is particularly preferable.

This aqueous solution can additionally be supplemented with a thickener (e.g., neutral polysaccharides), viscosity agent, sweetening agent, antiseptic, flavor, gelling agent, and so on.

The agent for enhancing a contrast of the present invention is, for example, sprayed, applied, or misted to the lumen of the digestive tract for use. Such spraying or application is preferably performed via a spraying tube or forceps channel included in an endoscope. In this context, the lumen of the digestive tract include: the upper digestive tract such as the stomach, intestinum duodenum, and esophagus; and the lower digestive tract such as the small intestine, colon, intestinum rectum, and anus. The agent for enhancing a contrast of the present invention exhibits particularly remarkable effects when used in the upper digestive tract. Therefore, the agent for enhancing a contrast is preferably used in the upper digestive tract, particularly preferably in the esophagus.

The agent for enhancing a contrast of the present invention enhances a contrast of an image of fluorescent staining of a lumen of the digestive tract with an intravenously administered fluorescent dye. In this context, any fluorescent dye may be used without particular limitations as long as it can stain the lumen of the digestive tract by intravenous administration; however, the fluorescent dye is preferably fluorescein or a salt thereof.

Fluorescent observation may be performed by measurement under irradiation with excitation lights. The fluorescent staining image is preferably observed by a fluorescence endoscope or an endoscope having a confocal imaging system.

More specifically, the agent for enhancing a contrast of the present invention is, for example, sprayed to a lumen of the digestive tract after the intravenous administration of a fluorescent dye. Then, the lumen of the digestive tract may be observed fluorescently.

EXAMPLES

Next, the present invention will be described more specifically with reference to Examples.

Example 1

Fluorescein is a fluorescent staining agent that has a staining property easily changed by the influence of a pH. The esophagus was excised from a mouse (ddY, 10-week-old, male). Immediately thereafter, fluorescein sodium (0.1 mg/mL) was administered thereto. The both ends of the excised esophagus were closed off to prevent the staining agent from running off. After a lapse of 3 minutes, the esophagus was washed with 0.1 M sodium phosphate buffer solution (pH 6), with its tubular form kept. The lumen was observed with a confocal microscope. FIG. 1 shows an image taken with the confocal microscope. The confocal microscope used was TCS SP2 manufactured by Leica Microsystems. The observation was conducted with a 20× lens under conditions involving a pinhole diameter of 1.00 airy (36.24 µm) and a gain value of 443.7 V.

The internal surface of the esophageal wall has a structure called the stratified squamous epithelium having many layers of cells and is therefore difficult to observe in a usual manner. However, staining with fluorescein sodium and the spraying of the acidic agent for enhancing a contrast of the present invention allow for observation using a confocal imaging system.

Example 2

The mouse esophagus was easily observed in an acidic state with a confocal imaging system by use of the agent for enhancing a contrast.

A mouse (ddY, 13-week-old, male) was fasted for 24 hours. Then, a small amount of 0.1 M sodium phosphate buffer solution (pH 4) was orally administered to the mouse to make its esophagus acidic.

Fluorescite (manufactured by Alcon Japan) was adjusted with a saline to 10 mg/mL, and a 300 μl aliquot thereof was perfused from the heart. Then, the esophagus was excised from the mouse. The pH value thereof was confirmed to be 5, which was acidic.

Figure 2:
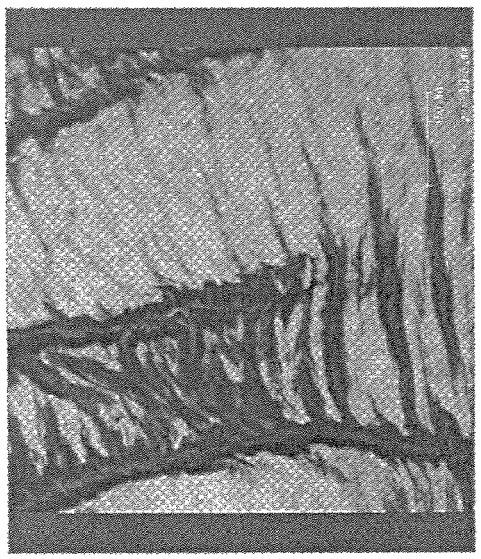
FIG. 2 is a diagram showing a confocal microscopic image of the esophagus before and after use of the agent for enhancing a contrast of the present invention.
Figure 2:
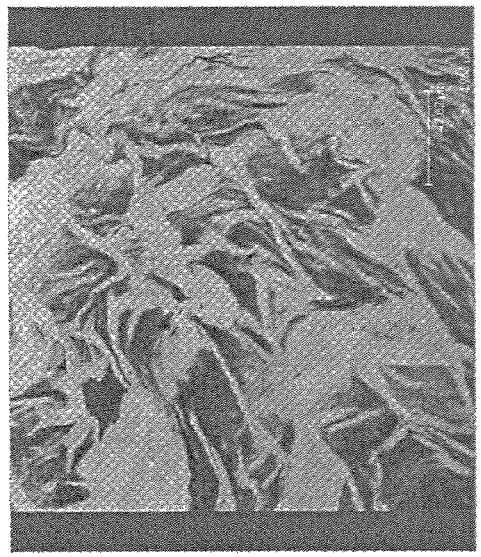
Figure 2:
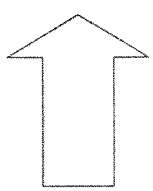
Figure 2:
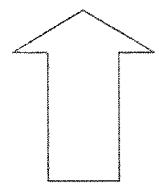
Figure 2:
Figure 2:
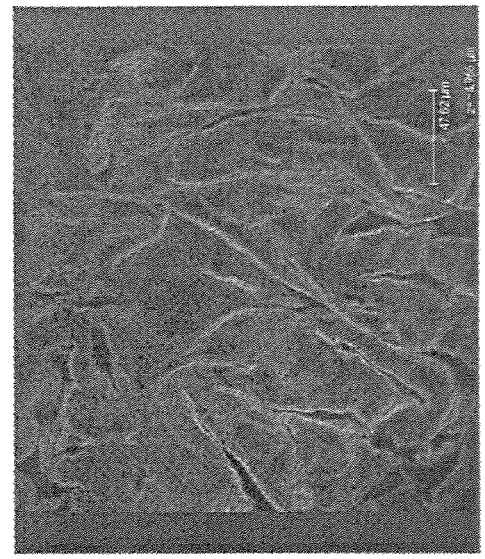

FIG. 2 shows an image taken with a confocal microscope (TCS SP2 manufactured by Leica Microsystems). The image was taken with a 20× lens under conditions involving a pinhole diameter of 1.00 airy (36.24 μm) and a gain value of 495.6 V.

The agent for enhancing a contrast (0.1 M sodium phosphate adjusted to pH 9) of the present invention was applied to an esophagus piece treated in the same way. Then, the esophagus piece was observed with a confocal microscope. The pH value thereof was confirmed to be 8, which was alkaline.

FIG. 2 shows an image taken therewith. The image was taken with a 20× lens under conditions involving a pinhole diameter of 1.00 airy (36.24 μm) and a gain value of 393.6 V.

The gain value was automatically set for the imaging. A smaller gain value (amplification factor) can give better determination.

The present Example showed that fluorescent observation using intravenous injection does not produce a clear staining image for observed sites in an acidic state (FIG. 2), whereas observation with a confocal imaging system is favorably performed inside a tissue adjusted to pH 8 by use of the agent for enhancing a contrast of the present invention (FIG. 2).

What is claimed is:

1. A method for enhancing a contrast of an image of fluorescent staining of a lumen of the digestive tract with an intravenously administered fluorescent dye, comprising applying an aqueous solution having a buffer capacity and having a pH of 6 to 10 to a lumen of the digestive tract after intravenous administration of the fluorescent dye; and adjusting the pH of the lumen of the digestive tract 6 to 10 when the lumen of the digestive tract is observed fluorescently.

2. The method for enhancing a contrast according to claim 1, wherein the lumen of the digestive tract is a lumen of the upper digestive tract.

3. The method for enhancing a contrast according to claim 1, wherein the aqueous solution having a buffer capacity has a pH of 6 to 8.

4. The method for enhancing a contrast according to claim 1, wherein the fluorescent dye is fluorescein or a salt thereof.

* * * * *